United States Patent [19]

Hartley et al.

[11] Patent Number: 5,204,113

[45] Date of Patent: Apr. 20, 1993

[54] PHARMACEUTICAL COMPOSITIONS CONTAINING PENTAMIDINE

[75] Inventors: Philip S. Hartley, Crich, England; John Stevens, Scarborough, Canada

[73] Assignee: Fisons plc, England

[21] Appl. No.: 657,335

[22] PCT Filed: Apr. 8, 1988

[86] PCT No.: PCT/GB88/00277

§ 371 Date: Nov. 14, 1988

§ 102(e) Date: Nov. 14, 1988

[87] PCT Pub. No.: WO88/07855

PCT Pub. Date: Oct. 20, 1988

Related U.S. Application Data

[63] Continuation of Ser. No. 275,054, Nov. 14, 1988, abandoned.

[30] Foreign Application Priority Data

Apr. 9, 1987 [GB] United Kingdom ............... 87/08527

[51] Int. Cl.$^5$ .......................... A61K 9/14; A61K 9/48; A61K 9/72
[52] U.S. Cl. .................................. 424/45; 128/203.15; 424/43; 424/452; 424/489; 514/636; 514/826; 514/951; 514/962
[58] Field of Search ................ 424/43, 452, 489, 454; 514/636, 951, 962, 826; 128/203.15

[56] References Cited

U.S. PATENT DOCUMENTS

| | | | |
|---|---|---|---|
| 3,870,046 | 3/1975 | Elliott | 128/203.15 |
| 3,888,253 | 6/1975 | Watt | 128/203.15 |
| 3,948,264 | 4/1976 | Wilke et al. | 128/203.15 |
| 3,957,965 | 5/1976 | Hartley | 424/452 |
| 4,013,075 | 3/1977 | Cocozza | 128/203.15 |
| 4,073,922 | 2/1978 | Wyburn-Mason | 514/825 |
| 4,119,723 | 10/1978 | Wyburn-Mason | 514/825 |
| 4,161,516 | 7/1979 | Bell | 424/451 |
| 4,324,794 | 4/1982 | Tidwell et al. | 514/387 |
| 4,397,863 | 8/1983 | Tidwell et al. | 514/415 |
| 4,399,151 | 8/1983 | Sjoersdma et al. | 514/663 |
| 4,402,965 | 9/1983 | Wyburn-Mason | 514/376 |
| 4,426,384 | 1/1984 | Wyburn-Mason | 514/825 |
| 4,546,113 | 10/1985 | Glazer | 514/636 |
| 4,563,468 | 1/1986 | Batchelor | 514/337 |
| 4,590,206 | 5/1986 | Forrester et al. | 514/826 |
| 4,619,942 | 10/1986 | Tidwell et al. | 514/636 |
| 4,649,911 | 3/1987 | Knight et al. | 128/200.21 |
| 4,681,752 | 7/1987 | Melillo | 424/453 |

(List continued on next page.)

FOREIGN PATENT DOCUMENTS 292100 11/1988 European Pat. Off. .
0292100 11/1988 European Pat. Off. .

(List continued on next page.)

OTHER PUBLICATIONS

DEBS C.A. 106:113175m (1987) Antimicrob. Agents Chemotherapy 31(1):37-41 (Jan. 1987).

DEBS C.A. 106: 219443n (1987) Am. Rev. Resp. Dis. 135(3): 731-737 (1987).

Meyer-Glauner C.A. 106: 169036j (1987) of DE 353349y, 19 Mar. 1987.

Hartley et al., C.A. 111:12537o (1989) of PCT WO (List continued on next page.)

Primary Examiner—Shep K. Rose
Attorney, Agent, or Firm—Marshall, O'Toole, Gerstein, Murray & Bicknell

[57] ABSTRACT

Pharmaceutical compositions suitable for administration by inhalation and containing pentamidine, or pharmaceutically acceptable salt thereof, in powder form. Such compositions include pressurized aerosol compositions and non-pressurized powder compositions. Also described is finely divided powdered pentamidine with a mass median diameter in the range 0.01 to 10 microns and a method for the prevention or treatment of pneumacystics carinii pneumonia which comprises administration by inhalation to a patient having or susceptible to that condition of a therapeutically effective quantity of pentamidine, or a pharmaceutically acceptable salt thereof, in powder form.

5 Claims, No Drawings

U.S. PATENT DOCUMENTS

| | | | |
|---|---|---|---|
| 4,752,425 | 6/1988 | Martin et al. | 424/1.1 |
| 4,781,871 | 11/1988 | West et al. | 424/1.1 |
| 4,823,784 | 4/1989 | Bordoni et al. | 128/200.14 |
| 4,956,355 | 9/1990 | Prendergast | 514/178 |
| 4,981,874 | 1/1991 | Latter et al. | 514/682 |
| 5,026,687 | 6/1991 | Yarchoan et al. | 514/45 |
| 5,106,837 | 4/1992 | Carson et al. | 514/46 |

FOREIGN PATENT DOCUMENTS

| | | |
|---|---|---|
| 309519 | 4/1989 | European Pat. Off. . |
| 3533494 | 3/1987 | Fed. Rep. of Germany . |
| M8142 | 8/1970 | France . |
| 8807855 | 10/1988 | PCT Int'l Appl. . |

OTHER PUBLICATIONS 8807855, 20 Oct. 1988 (G.B. 9 Apr. 1987, 24 pp.).

Bernard et al., C.A. 111:12540z (1989) of EP 292100, 23 Nov. 1988 (U.S. Ser. No. 30873, 26 Mar. 1987, 5 pp.).

S. Drake et al., *Clin. Pharm.*, 1985, 4, 507, "Pentamidine Isethionate in the Treatment of *Pneumocystic carinii* Pneumonia."

A. B. Montgomery et al., *The Lancet*, 1987, 2, 480, "Aerosolised Pentamidine as Sole Therapy for Pneumocystic Carinii Pneumonia in Patients with Acquired Immunodeficiency Syndrome."

A. J. Jesuthasan et al., Ibid., 971, "Aerosolised Pentamidine." (1987).

A. Heley, Ibid, 1092, "Aerosolised Pentamidine Treatment at Home." (1987).

E. M. Bernard et al., *Abs. Ann. Meet. of Am. Soc. Microbiol.*, 1986, 86, 14, "Abstracts of the Annual Meeting—1986."

PHARMACEUTICAL COMPOSITIONS CONTAINING PENTAMIDINE

This application is a continuation, of application Ser. No. 07/275,054, filed Nov. 14, 1988 now abandoned.

PHARMACEUTICAL COMPOSITIONS CONTAINING PENTAMIDINE

This invention relates to pharmaceutical compositions containing pentamidine in powdered form and suitable for administration by inhalation.

BACKGROUND TO THE INVENTION

Pneumo-cystis carinii pneumonia (PCP) is commonly contracted by patients suffering from acquired immunodeficiency syndrome (AIDS) and also by cancer and organ transplant patients. It has been estimated that some 65% of AIDS patients develop PCP. Amongst such patients the condition is life-threatening.

1,5-Di(4-amidinophenoxy)pentane, which is generically known as pentamidine, has for many years been known for use as a pharmaceutical, in particular for the treatment of the early stages of African trypanosomiasis ('sleeping sickness'). Pentamidine has also been found to be effective in the treatment of PCP infection in AIDS patients when administered by intravenous infusion or intramuscular injection although this treatment is often accompanied by severe side-effects, e.g. hypotension, renal failure and hypoglycaemia. More recently, there has been a report (Abstracts of the Annual Meeting of the American Society of Microbiology 86,14 (1986)) of the prevention of PCP by inhalation of an aerosol spray containing pentamidine or a pharmaceutically acceptable salt thereof. This report, however, relates only to aerosols formed by nebulisation of aqueous solutions.

We have now surprisingly found that pentamidine is effective in the prevention or treatment of PCP when administered by inhalation in powdered form and that formulation of the drug in this way offers certain advantages.

SUMMARY OF THE INVENTION

According to the invention we provide a pharmaceutical composition suitable for administration by inhalation and containing pentamidine, or a pharmaceutically acceptable salt thereof (hereinafter referred to as the active ingredient), in powder form.

Pharmaceutically acceptable salts of pentamidine which may be mentioned are the isethionate, the naphthoate and the mesylate.

We also provide finely divided pentamidine with a mass median diameter in the range 0.01 to 10 microns.

According to another aspect of the invention, there is provided a method for the prevention or treatment of PCP which comprises administration by inhalation to a patient having or susceptible to that condition of a therapeutically effective quantity of pentamidine, or a pharmaceutically acceptable salt thereof, in powder form.

According to another aspect of the invention, there is provided the use of pentamidine, or a pharmaceutically acceptable salt thereof, as active ingredient in the manufacture of a medicament for use in the treatment of PCP, characterized in that the medicament contains pentamidine in powdered form.

DETAILED DESCRIPTION OF THE INVENTION

The composition according to the invention may be a non-pressurised powder composition or a pressurised aerosol composition containing a pharmaceutically acceptable liquefied gas aerosol propellant.

For pressurised aerosol compositions, the active ingredient is preferably finely divided, e.g. having a mass median diameter in the range 0.01 to 10 microns. We particularly prefer the active ingredient to have a mass median diameter of less than 4 microns and especially of less than 3.0 microns and most preferably of less than 2.8 microns. We also prefer not more than 5% by weight of the particles to have a diameter of greater than 10 microns, and more preferably not less than 90% by weight of the particles to have a diameter of less than 6 microns.

We prefer pressurised aerosol compositions to contain from 0.5 to 12%, more preferably from 0.5 to 10%, and most preferably from 0.5 to 5%, e.g. about 1 to 3.5% by weight of finely divided active ingredient.

By mass median diameter we mean the diameter such that half the particulate mass is in particles of lesser diameter and half in particles of greater diameter. The mass median diameter is essentially a Stokes diameter and may be determined using a Joyce Loebl sedimentation disc centrifuge either in a two layer or line start photometric mode (Bagness J and Ottaway A, Proc. Soc. Analyt. Chem. Part 4, Vol 9, 1972 pages 83–86).

The active ingredient of mass median diameter less than 4 microns when formulated as aerosol units and when the units are examined using a single stage liquid impinger (modification of that described in J. Pharm. Pharmac. 1973, 25, Suppl. 32P-36P) produces a greater dispersion than exactly analogous units containing active ingredient of larger mass median diameter. The single stage liquid impinger samples the whole cloud delivered from the aerosol and separates it into two fractions by inertial impaction. The fraction of smaller particle size is less than 10 microns in aerodynamic diameter and represents material which is likely to penetrate into the deeper regions of the human airways.

By providing a large proportion of fine particles of active ingredient the invention enables a lower dosage of drug to be administered and/or for an equivalent amount of drug to produce a greater or longer lasting effect.

The fine active ingredient may be made by grinding or milling and is preferably dried thoroughly before it is incorporated into the liquefied propellant medium.

The liquefied propellant medium, and indeed the total composition, is preferably such that the active ingredient does not dissolve therein to any substantial extent.

The liquefied propellant is preferably a gas at room temperature (20° C.) and atmospheric pressure i.e. it should have a boiling point below 20° C. at atmospheric pressure. The liquefied propellant should also be non-toxic. Among the suitable liquefied propellants which may be employed are dimethyl ether and alkanes containing up to five carbon atoms, e.g. butane or pentane, or a lower alkyl chloride, e.g. methyl, ethyl or propyl chlorides. The most suitable liquefied propellants are the fluorinated and fluorochlorinated lower alkanes such as are sold under the Registered Trade Mark 'Freon'. Mixtures of the above mentioned propellants may suitable be employed. Examples of these propellants are dichlorodifluoromethane ('Propellant 12'),
1,2-dichlorotetrafluoroethane ('Propellant 114')
trichloromonofluoromethane ('Propellant 11'),
dichloromonofluoromethane ('Propellant 21'),
monochlorodifluoromethane ('Propellant 22'),
trichlorotrifluoroethane ('Propellant 113'), and
monochlorotrifluoromethane ('Propellant 13').
Propellants with improved vapour pressure characteristics may be obtained by using certain mixtures of these compounds, e.g. 'Propellant 11' with 'Propellant 12', or 'Propellant 12' with 'Propellant 114'. For example, 'Propellant 12', which has a vapour pressure of about 570 kPa (absolute) at 20° C. and 'Propellant 114', with a vapour pressure of about 180 kPa (absolute) at 20° C., may be mixed in various proportions to form a propellant having a desired intermediate vapour pressure. We prefer compositions which do not contain trichloromonofluoromethane.

It is desirable that the vapour pressure of the propellant employed be between 380 and 500, and preferably between 410 and 470 kPa (absolute) at 20° C. Such a propellant mixture is usable safely with metal containers. Other mixtures of 'Propellant 12' with 'Propellant 114', or of 'Propellant 12' with 'Propellant 11', or of 'Propellant 12' with 'Propellant 11' and 'Propellant 114' with absolute vapour pressures at 20° C. in the range 230 to 380 kPa are usable safely with specially reinforced glass containers.

The pressurised aerosol composition may also contain a surface active agent. The surface active agent may be a liquid or solid non-ionic surface active agent or may be a solid anionic surface actice agent. It is preferred to use the solid anionic surface active agent in the form of the sodium salt.

The preferred solid anionic surface active agent is sodium dioctyl-sulphosuccinate.

The amount of the surface active agent required is related to the solids content of the composition and to the particle size of the solids. In general it is only necessary to use 5-15%, and preferably 5-8%, of the solid anionic surface active agent by weight of the solids content of the composition. We have found that, under certain conditions, use of a solid anionic surface active agent gives a better dispersion of medicament when the composition is released from a pressurised pack than does the use of a liquid non-ionic surface active agent.

When a liquid non-ionic surface-active agent is employed it should have an hydrophile-lipophile balance (HLB) ratio of less than 10. The HLB ratio is an empirical number which provides a guide to the surface-active properties of a surface-active agent. The lower the HLB ratio, the more lipophilic is the agent, and conversely, the higher the HLB ratio, the more hydrophilic is the agent. The HLB ratio is well known and understood by the colloid chemist and its method of determination is described by W C Griffin in the Journal of the Society of Cosmetic Chemists, Vol 1, No 5, pages 311-326 (1949). Preferably the surface-active agent employed should have an HLB ratio of 1 to 5. It is possible to employ mixtures of surface-active agents, the mixture having an HLB ratio within the prescribed range.

Those surface-active agents which are soluble or dispersible in the propellant are effective. The more propellant-soluble surface-active agents are the most effective.

We prefer the liquid non-ionic surface-active agent to comprise from 0.1 to 2%, and more preferably from 0.2 to 1%, by weight of the total composition. Such compositions tend to be more physically stable on storage.

Among the liquid non-ionic surface-active agents which may be employed are the esters or partial esters of fatty acids containing from 6 to 22 carbon atoms, such as caproic, octoic, lauric, palmitic, stearic, linoleic, linolenic, oleostearic and oleic acids with an aliphatic polyhydric alcohol or its cyclic anhydride such as, for example, ethylene glycol, glycerol, erythritol, arabitol, mannitol, sorbitol, the hexitol anhydrides derived from sorbitol (the sorbitan esters sold under the Registered Trade Mark 'Span') and the polyoxyethylene and polyoxypropylene derivatives of these esters. Mixed esters, such as mixed or natural glycerides, may be employed. The preferred liquid non-ionic surface-active agents are the oleates of sorbitan, e.g. those sold under the Registered Trade Marks 'Arlacel C' (Sorbitan sesquioleate), 'Span 80' (Sorbitan monooleate) and 'Span 85' (Sorbitan trioleate). Specific examples of other liquid non-ionic surface-active agents which may be employed are sorbitan monolaurate, polyoxyethylene sorbitol tetraoleate, polyoxyethylene sorbitol pentaoleate, and polyoxypropylene mannitol dioleate. A solid non-ionic surface active agent which may be mentioned is lecithin, e.g. soya lecithin, a vegetable lecithin extracted from soya beans, but lecithin is not preferred.

We particularly prefer pressurised aerosol compositions containing a sorbitan or sorbitol ester, e.g. sorbitan trioleate, in a mixture of propellants 12 and 114. We prefer the ratio of propellant 12 to 114 to be in the range 2 to 1:1, and preferably about 1.5:1 by weight, i.e. we prefer an excess of propellant 12 over propellant 114.

We also prefer the total water content of the composition to be in the range of 500 to 3,500 ppm. The composition when initially made preferably has a water content at the lower end of this range, but the water content tends to rise on storage.

We prefer packages containing from about 8 to 30 ml of composition, e.g. a conventional aerosol pressure pack of 10 ml. The pack preferably has a valve adapted to deliver unit dosages of between 0.025 and 0.25 ml, and preferably 0.05 or 0.1 ml, of composition. We prefer the valve to deliver 1, 2, 3, 4 or 5 mg of active ingredient and unit doses of these quantities of the drug are provided.

Pressurised aerosol compositions of the invention may be made by mixing the various components at a temperature and pressure at which the propellant is in the liquid phase and the active ingredient is in the solid phase.

In producing the pressurised aerosol compositions and packages of the invention, a container equipped with a valve is filled with a propellant containing the finely-divided active ingredient in suspension. A container may first be charged with a weighed amount of dry active ingredient which has been ground to a predetermined particle size, or with a slurry of powder in the cooled liquid propellant. A container may also be filled by introducing powder and propellant by the normal cold filling method, or a slurry of the powder in that component of the propellant which boils above room temperature may be placed in the container, the valve sealed in place, and the balance of the propellant may be introduced by pressure filling through the valve nozzle. As a further alternative a bulk of the total composition may be made and portions of this bulk composition may be filled into the container through the valve. Throughout the preparation of the product care is desirably exercised to minimise the absorption of moisture. On operating the valve, the powder will be dispensed in a stream of propellant, which will vaporise providing an aerosol of dry powder.

In non-pressurised powder compositions the active ingredient in finely divided form may be used in admixture with a larger sized carrier comprising particles, e.g. of up to 400 microns diameter. We prefer at least 90% by weight of the particles of the active ingredient to have an effective particle size below 10 microns (and preferably of from 0.01 to 10 microns), and at least 90% by weight of the particles of the carrier to have an effective particle size below 400 microns, and at least 50% by weight of the particles of the carrier to have an effective particle size above 30 microns. Effective particle size for particles below 30 microns may be measured by a Coulter counter. Effective particle size for particles above 30 microns may be measured by an Alpine air jet sieve.

Desirably, at least 95% by weight of the particles of the active ingredient have an effective particle size in the range 0.01 to 10 microns. Preferably at least 90%, and more desirably at least 95%, by weight thereof have an effective particle size in the range 1 to 10 microns. Suitably, at least 50% by weight of the particles of the active ingredient have an effective particle size in the range 2 to 6 microns.

The particle size spectrum of the carrier will depend on the particular inhalation device from which the formulation is to be dispersed. It is however desirable to avoid carrier particles of less than 10 microns in size, thus minimising the number of non-drug particles which penetrate deep into the lung. A large proportion of very large particles may also cause a gritty feel in the mouth of the user and is therefore less preferred. Use of a carrier of large particle size may also cause problems in filling when using filling machines which involve a dosator which picks up powder by dipping into a powder bed from above. However, use of a carrier of large particle size may ease filling when using machines in which a die is filled from above, but may incline the composition to segregate during transport or storage. Thus, desirably, at least 95% by weight of the particles of carrier have an effective particle size below 400 microns. Preferably at least 50%, and more desirably at least 70%, by weight of the carrier particles have an effective particle size in the range 30 to 150, especially 30 to 80, microns.

Non-pressurised powder compositions preferably contain from 2 to 50% by weight, more especially from 5 to 25% by weight, and particularly from 10 to 15% by weight of the active ingredient, and from 50 to 98% by weight, more especially from 75 to 95% by weight and particularly from 85 to 90% by weight of the carrier.

The finely divided active ingredient may be prepared in the desired particle size range for example using a ball mill, a fluid energy mill, by precipitation or by spray drying. The carrier may be prepared by spray drying or grinding and subsequently separating out the desired fraction, for example by air classification and/or sieving.

The non-pressurised powder compositions may be prepared by mixing the ingredients together in one or, preferably, more (e.g. two) steps in a mixer, such as a planetary or other stirred mixer.

The carrier may be any non-toxic material which is chemically inert to the active ingredient and is acceptable for inhalation. Examples of carriers which may be used include inorganic salts, e.g. sodium chloride or calcium carbonate; organic salts, e.g. sodium tartrate or calcium lactate; organic compounds, e.g. urea or propylidone; monosaccharides, e.g. lactose, mannitol, arabinose or dextrose monohydrate; disaccharides, e.g. maltose or sucrose; polysaccharides, e.g. starches, dextrins or dextrans. A particularly preferred carrier is lactose, e.g. crystalline lactose.

The non-pressurised powder compositions will generally be put up in sealed gelatine, plastic or other capsules. The container is preferably loosely filled to less than about 80% by volume, preferably less than about 50% by volume, with the powder composition.

Alternatively, the active ingredient may be used in pellet or granule form, wherein the pellet or granule is soft, is from 10 to 1,000, preferably 30 to 500, microns in diameter and comprises an agglomeration of individual medicament particles, at least 90% by weight of which have a diameter of less than 10 microns.

The soft pellet or granule preferably has an internal coherence such that the pellet or granule remains intact when filled into a container, e.g. a capsule, using automatic or semi-automatic filling machines, under conditions of transport and storage, and when fluidised within a container in the device from which it is intended to dispense the pellets or granules and yet may be broken up into particles of a therapeutically effective size outside the container as it discharges from the container.

We have found that satisfactory soft pellets or granules for use in insufflators of the type described in British Patent No 1,182,779 (commercially available under the Registered Trade Mark 'Spinhaler') and powered by human inhalation have a mean size in the range of from 50 to 250 microns, preferably a mean size in the range 120 to 160 microns and most preferably a mean size of about 140 microns.

The compositions of the invention are particularly useful in the prophylactic or remedial treatment, e.g. the inhalation treatment, of pneumo-cystis carinii pneumonia and other infectious conditions of the airways, such as are frequently encountered in association with acquired immunodeficiency syndrome (AIDS). The treatment may be by oral or nasal inhalation and is preferably treatment of man.

The compositions of the invention are advantageous in that they are more convenient for the patient to use, in that they are more stable, and in that lower dosages of active ingredient can be used (thus reducing or substantially avoiding any possible side-effects) when compared to other known formulations of the active ingredient.

The dosage to be given will clearly vary with the patient and with their condition. However for patients who are infected with pneumonia a dosage of 20 to 50 mg given every 1 to 3 weeks may be used. We have, however, surprisingly found that more frequent lower doses of powder compositions, e.g. 1 to 5 mg of active ingredient daily, are also effective, particularly for prophylactic use. We particularly prefer a treatment regime in which frequent, e.g. daily, low doses, e.g. 1 to 5 mg of active ingredient, are administered as pressurised aerosol compositions.

The invention is illustrated, but in no way limited by the following Examples.

EXAMPLE 1

| Pressurised Aerosol Formulation | |
|---|---|
| Ingredients | |
| Pentamidine isethionate mass median diameter less than 3 microns | 0.270 |
| Sorbitan trioleate | 0.091 |
| Propellant 114 | 7.099 |
| Propellant 12 | 10.649 |
| | 18.109 |

Method

The sorbitan ester is dispersed in up to half the propellant 12 at −40° C. while stirring with a high dispersion mixer. The active ingredient is added to the resulting dispersion and disperses in it very readily. The balance of the propellant 12 is then added at −50° C., followed by the propellant 114 also cooled to −50° C. The resulting mixtures are then filled into vials onto which valves, e.g. metering valves, are subsequently crimped.

EXAMPLE 2

| Non-Pressurised Powder Formulation | |
|---|---|
| Ingredients | |
| Pentamidine isethionate particle size 0.01–10 microns | 20 mg |
| Lactose particle size 30–80 microns | 20 mg |

Method

The pentamidine isethionate and the lactose are intimately mixed and then filled into a hard gelatine capsule.

We claim:

1. A sealed capsule loosely filled with a nonpressurized dry powder pharmaceutical composition for the prophylactic or remedial treatment of pneumono-cystis carinii pneumonia by oral or nasal inhalation, said composition containing as active ingredient, finely divided pentamidine or a pharmaceutically acceptable salt thereof with a mass median diameter of 0.01 to 10 microns.

2. A composition according to claim 1, wherein the active ingredient is in admixture with a pharmaceutically acceptable carrier.

3. A composition according to claim 1 which contains from 2 to 50% by weight active ingredient.

4. A composition according to claim 1, wherein at least 95% by weight of the particles of active ingredient have an effective particle size of from 0.01 to 10 microns.

5. A method for the prevention or treatment of pneumono-cystis carinii pneumonia which comprises administration by oral or nasal inhalation of a therapeutically effective quantity of a dry powder composition in accordance with claim 1, to a patient having or susceptible to that condition.

* * * * *